United States Patent

Yuan et al.

[11] Patent Number: 5,892,041
[45] Date of Patent: Apr. 6, 1999

[54] FUSED INDOLECARBOXAMIDES: DOPAMINE RECEPTOR SUBTYPE SPECIFIC LIGANDS

[75] Inventors: Jun Yuan, Clinton; Jan William Francis Wasley, Madison, both of Conn.

[73] Assignee: Neurogen Corporation, Branford, Conn.

[21] Appl. No.: 695,712

[22] Filed: Aug. 12, 1996

[51] Int. Cl.$^6$ ............... C07D 403/12; C07D 403/14; C07D 401/12; C07D 401/14
[52] U.S. Cl. ............... 544/372; 544/295; 544/363; 544/364; 546/167; 546/175; 546/200; 546/276.7; 548/441; 548/448
[58] Field of Search ............... 544/295, 363, 544/364, 372

[56] References Cited

U.S. PATENT DOCUMENTS

| 3,932,456 | 1/1976 | Albrecht et al. | 548/441 |
| 5,395,835 | 3/1995 | Glase et al. | 514/254 |

FOREIGN PATENT DOCUMENTS

WO 94/14773   7/1994   WIPO .

OTHER PUBLICATIONS

Murray, P. John, et al., "A Novel Series of Arylpiperazines With High Affinity and Selectivity For The Dopamine $D_3$ Receptor," *Bioorg. & Med. Chem. Let.*, 5(3), 219–222 (1995).

Sokoloff, Pierre, et al., "Molecular cloning and characterization of a novel dopamine receptor ($D_3$) as a target for neuroleptics," *Nature*, 347, 146–151 (Sep. 13, 1990).

*Primary Examiner*—Emily Bernhardt
*Attorney, Agent, or Firm*—McDonnell, Boehnen Hulbert & Berghoff

[57] ABSTRACT

Disclosed are compounds of the formula:

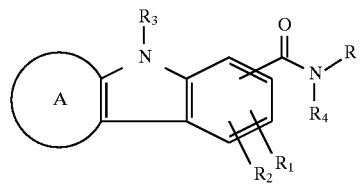

or the pharmaceutically acceptable acid addition salts thereof wherein:

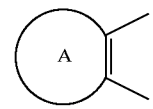

represents an aromatic or alicyclic ring;

$R_1$ and $R_2$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —$SO_mR'$, where R' is $C_1$–$C_6$ alkyl and wherein m is 0, 1 or 2; or $R_1$ and $R_2$ independently represent —CONR'R", or —NR'R" where R' and R" independently represent hydrogen or $C_1$–$C_6$ alkyl;

$R_3$ is hydrogen, $C_1$–$C_6$ alkyl, or —COR'" where R'" is $C_1$–$C_6$ alkyl;

$R_4$ is hydrogen or $C_1$–$C_6$ alkyl; and

R represents an aminoalkyl group, which compounds are useful in the treatment of affective disorders such as schizophrenia, depression, Alzheimer's disease, movement disorders such as Parkinsonism and dystonia, and other disorders which respond to dopaminergic blockade such as substance abuse and obsessive compulsive disorders. Further, compounds of this invention are useful in treating the extrapyramidal side effects associated with the use of conventional neuroleptic agents.

25 Claims, No Drawings

FUSED INDOLECARBOXAMIDES: DOPAMINE RECEPTOR SUBTYPE SPECIFIC LIGANDS

BACKGROUND OF THE INVENTION

1. Field of the invention

This invention relates to indolecarboxamide derivatives which selectively bind to brain dopamine receptor subtypes. More specifically, it relates to fused indolecarboxamides such as carbozolecarboxamides, tetrahydrocarbazolecarboxamides, and fused cycloalkylindolecarboxamides, and to pharmaceutical compositions comprising such compounds. It further relates to the use of such compounds in the treatment or prevention of various neuropsychochological disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_3$ receptor subtype has recently been identified (Sokoloff et al., Nature, 347, 146 (1990)). Its unique localization in limbic brain areas and its differential recognition of various antipsychotics suggest that the $D_3$ receptor may play a major role in the etiology of schizophrenia. Selective $D_3$ antagonists may be effective antipsychotics free from the neurological side effects displayed by conventional neuroleptics. Compounds of the present invention demonstrate high affinity and selectivity in binding to the $D_3$ receptor subtype. They may be of potential use in treatment of schizophrenia, psychotic depression and mania. Other dopamine-mediated diseases such as Parkinsonism and tardive dyskinesias may also be treated directly or indirectly by modulation of $D_3$ receptors.

U.S. Pat. No. 5,395,835 discloses N-aminoalkyl-2-napthalamides said to have affinity at dopamine $D_3$ receptors. The compounds of the present invention differ significantly from this prior art in that they possess a dibenzofurancarboxamide substructure.

U.S. Pat. No. 3,932,456 discloses compounds of the formula:

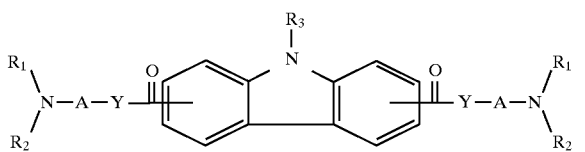

wherein each of $R_1$ and $R_2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or $R_1$ and $R_2$ taken together with the nitrogen atom to which they are attached is pyrrolidino, piperidino, N-(lower)alkylpiperazino, or morpholino; each A is alkylene of 2 to about 8 carbon atoms and separates its adjacent Y and amino nitrogen by an alkylene chain of at least 2 carbon atoms; each Y is oxygen, or N-R wherein R is hydrogen, methyl or ethyl; and $R_3$ is hydrogen or (lower) primary or secondary alkyl; or a pharmaceutically acceptable acid addition salt thereof.

These compounds are said to be useful as pharmaceuticals for preventing or inhibiting a viral infection.

International application WO94/14773 discloses compounds said to have affinity for the 5-$HT_1$-like receptor and utility in the treatment of migraine. The compounds disclosed in that application have the following formula:

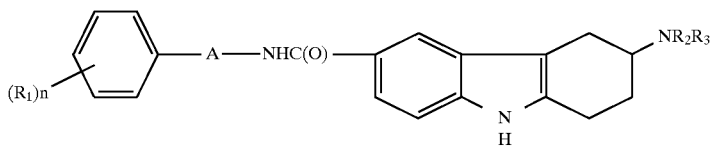

wherein $R_1$ represents halogen, $C_{1-4}$ alkyl, $C_{1-4}$ alkoxy, hydroxy, $NO_2$, $-NR_4R_5$, $R_4R_5NCO(CH2)_m-$, $R_4R_5NSO_2(CH2)_m-$, $R_6CONH(CH2)_m-$ or $R_7SO_2(CH2)_m-$; $R_4$ and $R_5$ each independently represent hydrogen or $C_{1-4}$ alkyl or $N_4R_5$ represents a 5- to 7-member heterocyclic ring; $R_6$ represents hydrogen or $C_{1-4}$ alkyl; $R_7$ represents $C_{1-4}$ alkyl; m is zero, 1, or 2; n is zero or 1 to 5; $R_2$ and $R_3$ each independently represent hydrogen, $C_{1-6}$ alkyl or benzyl or $-NR_2R_3$ represents a pyrrolidino, piperidino or hexahydroazepino ring; and A represents a bond, a $C_{1-5}$ alkylene chain or a $C_{3-5}$ alkenyl chain wherein the double bond is not adjacent the nitrogen atom.

Murray et al., Bioorg. Med. Chem. Let., 5: 219 (1995), describe 4-carboxamidobiphenyls said to have affinity at dopamine $D_3$ receptors.

SUMMARY OF THE INVENTION

This invention provides novel compounds of Formula I which interact with dopamine receptor subtypes. Thus, the invention provides compounds of general Formula I useful in the treatment and/or prevention of various neuropsychological disorders. The invention also provides pharmaceutical compositions comprising compounds of Formula 1.

The invention further relates to the use of such compounds and compositions in the treatment of affective disorders such as schizophrenia, depression, Alzheimer's disease and certain movement disorders such as Parkinsonism and dystonia. Compounds of this invention are also useful in treating the extrapyramidal side effects associated with the use of conventional neuroleptic agents. Further, the compounds of the present invention are useful for the treatment of other disorders which respond to dopaminergic blockade such as substance abuse and obsessive compulsive disorder.

Since dopamine $D_3$ receptors are concentrated in the limbic system (Taubes, Science, 265: 1034 (1994)) which controls cognition and emotion, compounds that interact with these receptors are also useful in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention which interact specifically with the dopamine $D_3$ receptor subtype.

Furthermore, the compounds of this invention are useful in treatment of depression, memory-impairment or Alzheimer's disease by modulation of $D_3$ receptors which selectively exist in limbic areas known to control emotion and cognitive functions. The compounds of the present invention are also useful for the treatment of other disorders that respond to dopaminergic blockade such as substance abuse (Caine and Koob, Science, 260: 1814 (1993)) and obsessive compulsive disorder (Goodman et al., Clin. Psychopharmacol., 7: 35 (1992). The compounds of the invention interact with dopamine receptor subtypes resulting in the pharmacological activity of these compounds.

Accordingly, a broad embodiment of the invention is directed to a compound of Formula I:

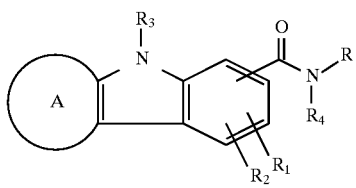

or the pharmaceutically acceptable acid addition salts thereof; wherein:

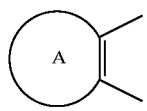

represents

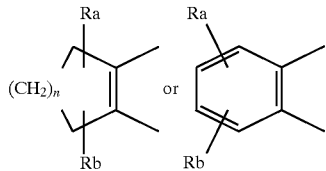

where $R_a$ and $R_b$ independently represent hydrogen, $C_1$–$C_6$ alkyl, hydroxy, $C_1$–$C_6$ alkoxy, or amino mono- or disubstituted with $C_1$–$C_6$ alkyl; and n is an integer from one to four;

$R_1$ and $R_2$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', or —$SO_mR'$, where R' is $C_1$–$C_6$ alkyl and where m is 0, 1 or 2; or $R_1$ and $R_2$ independently represent —CONR'R" or —NR'R" where R' and R" independently represent hydrogen or $C_1$–$C_6$ alkyl;

$R_3$ is hydrogen, $C_1$–$C_6$ alkyl, or —COR''' where R''' is $C_1$–$C_6$ alkyl;

$R_4$ is hydrogen or $C_1$–$C_6$ alkyl; and

R represents an aminoalkyl group.

Thus, the invention relates to the use of compounds of formula I in the treatment and/or prevention of neuropsychochological disorders including, but not limited to, schizophrenia, mania, dementia, depression, anxiety, compulsive behavior, substance abuse, memory impairment, cognitive deficits, Parkinson-like motor disorders and motion disorders related to the use of neuroleptic agents.

DETAILED DESCRIPTION OF THE INVENTION

In addition to compounds of general formula I described above, the invention encompasses compounds of general formula IA:

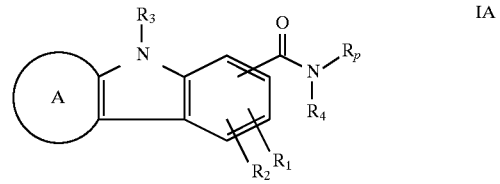

wherein
the A ring, $R_1$, $R_2$, $R_3$, and $R_4$ are as defined above for Formula I; and
$R_p$ represents an aminoalkyl group of the formula

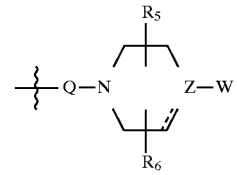

where
Q represents an alkylene group of 2 to 6 carbon atoms optionally substituted with one or more alkyl groups having from 1 to 4 carbon atoms;
Z is N or C;
$R_5$ and $R_6$ are the same or different and represent hydrogen or $C_1$–$C_6$ alkyl; or
$R_5$ and $R_6$ together with the the 6-membered ring to which they are attached form a 5 to 8-membered ring; and
W is phenyl, naphthyl, 1-(5,6,7,8-tetrahydro)naphthyl or 4-(1,2-dihydro)indenyl, quinolinyl, pyridinyl, pyrimidyl, isoquinolinyl, benzofuranyl, or benzothienyl, each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

Preferred compounds of Formula IA include those where $R_1$–$R_4$ are hydrogen or alkyl and Q is alkylene of 3–5 carbon atoms. Other preferred compounds of Formula IA are those where $R_1$ and $R_2$ are hydrogen, $R_3$ is hydrogen or alkyl, more preferably hydrogen or methyl, $R_4$ is hydrogen, methyl, or ethyl, and Q is alkylene of 3–5 carbon atoms.

In addition to compounds of general Formula I described above, the invention encompasses compounds of general Formula IB:

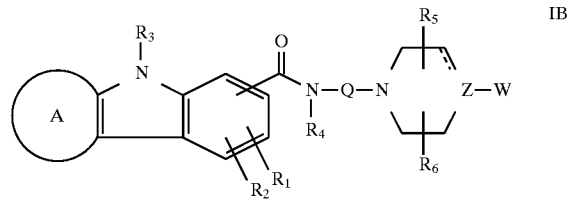

wherein:
the A ring and $R_1$–$R_6$ are as defined above for Formula IA; and
Q, Z and W are as defined above.

The present invention further encompasses compounds of Formula II:

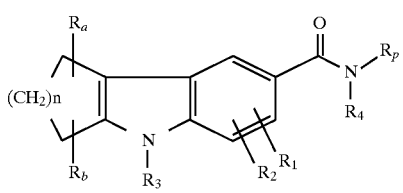

where $R_a$, $R_b$, n, $R_p$, and $R_1$–$R_4$ are as defined above for Formula IA.

Preferred compounds of Formula II include those where $R_1$–$R_4$ are hydrogen or alkyl, $R_a$ and $R_b$ are hydrogen, and Q is alkylene of 3–5 carbon atoms. Other preferred compounds of Formula II are those where $R_a$ and $R_b$ are hydrogen, $R_1$ and $R_2$ are hydrogen, $R_3$ is hydrogen or alkyl, more preferably hydrogen or methyl, $R_4$ is hydrogen, methyl, or ethyl, Q is alkylene of 3–5 carbon atoms, more preferably butylene, and W is quinolinyl, naphthyl, or phenyl optionally substituted with up to two substituents independently selected from halogen, $C_1$–$C_4$ alkyl, and $C_1$–$C_4$ alkoxy. In more preferred compounds of Formula II, Z is nitrogen, and W is quinolinyl, naphthyl, or phenyl optionally substituted with up to two groups in the 2 and/or 3 positions (relative to the point of attachment of the phenyl group to the piperazine ring), the groups being independently selected from halogen, $C_1$–$C_4$ alkyl, and $C_1$–$C_4$ alkoxy. Particularly preferred W groups of Formula II are those where W is naphthyl or phenyl optionally substituted with up to two groups in the 2 and/or 3 positions (relative to the point of attachment of the phenyl group to the piperazine ring), the groups being independently selected from chloro, methyl, and methoxy.

The present invention further encompasses compounds of Formula III:

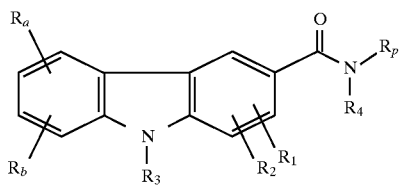

where $R_a$, $R_b$, $R_p$, and $R_1$–$R_4$ are as defined above for Formula IA.

Preferred compounds of Formula III include those where $R_1$–$R_4$ are hydrogen or alkyl, $R_a$ and $R_b$ are hydrogen, and Q is alkylene of 3–5 carbon atoms. Other preferred compounds of Formula III are those where $R_a$ and $R_b$ are hydrogen, $R_1$ and $R_2$ are hydrogen, $R_3$ is hydrogen or alkyl, more preferably hydrogen or methyl, $R_4$ is hydrogen, methyl, or ethyl, Q is alkylene of 3–5 carbon atoms, more preferably butylene, and W is quinolinyl, naphthyl, or phenyl optionally substituted with up to two substituents independently selected from halogen, $C_1$–$C_4$ alkyl, and $C_1$–$C_4$ alkoxy. In more preferred compounds of Formula III, Z is nitrogen, and W is quinolinyl, naphthyl or phenyl optionally substituted with up to two groups in the 2 and/or 3 positions (relative to the point of attachment of the phenyl group to the piperazine ring), the groups being independently selected from halogen, $C_1$–$C_4$ alkyl, and $C_1$–$C_4$ alkoxy. Particularly preferred W groups of Formula III are those where W is naphthyl or phenyl optionally substituted with up to two groups in the 2 and/or 3 positions (relative to the point of attachment of the phenyl group to the piperazine ring), the groups being independently selected from chloro, methyl, and methoxy.

The invention also provides compounds of Formula IV

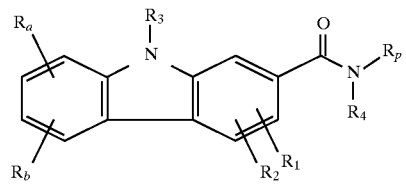

where $R_a$, $R_b$, $R_p$, and $R_1$–$R_4$ are as defined above for Formula IA.

Preferred compounds of Formula IV include those where $R_1$–$R_4$ are hydrogen or alkyl, $R_a$ and $R_b$ are hydrogen, and Q is alkylene of 3–5 carbon atoms. Other preferred compounds of Formula IV are those where $R_a$ and $R_b$ are hydrogen, $R_1$ and $R_2$ are hydrogen, $R_3$ is hydrogen or alkyl, more preferably hydrogen or methyl, $R_4$ is hydrogen, methyl, or ethyl, Q is alkylene of 3–5 carbon atoms, more preferably butylene, and W is quinolinyl, naphthyl, or phenyl optionally substituted with up to two substituents independently selected from halogen, $C_1$–$C_4$ alkyl, and $C_1$–$C_4$ alkoxy. In more preferred compounds of Formula IV, Z is nitrogen, and W is quinolinyl, naphthyl or phenyl optionally substituted with up to two groups in the 2 and/or 3 positions (relative to the point of attachment of the phenyl group to the piperazine ring), the groups being independently selected from halogen, $C_1$–$C_4$ alkyl, and $C_1$–$C_4$ alkoxy. Particularly preferred W groups of Formula IV are those where W is naphthyl or phenyl optionally substituted with up to two groups in the 2 and/or 3 positions (relative to the point of attachment of the phenyl group to the piperazine ring), the groups being independently selected from chloro, methyl, and methoxy.

When a compound of the invention is obtained as a mixture of enantiomers, these enantiomers can be separated, when desired, by conventional methods such as crystallization in the presence of a resolving agent, or chromatography, for example using a chiral HPLC column.

Representative compounds of the present invention, which are encompassed by Formula I, include, but are not limited to, the compounds shown in Table 1 below and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC$—$(CH_2)_n$—$COOH$ where n is 0–4, and the like. Those skilled in the art will recognize a wide variety of non-toxic pharmaceutically acceptable addition salts.

The present invention also encompasses prodrugs, e.g., acylated prodrugs, of the compounds of Formula I. Those skilled in the art will recognize various synthetic methodologies which may be employed to prepare non-toxic pharmaceutically acceptable addition salts and prodrugs of the compounds encompassed by Formula I.

The following numbering system is used to identify positions on the carbazole ring portion of the compounds of the invention:

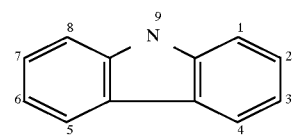

The following numbering system is used to identify positions on the tetrahydrocarbazole-ring portion of the compounds of the invention:

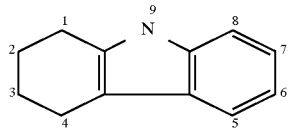

The following numbering system is used to identify positions on the tetrahydrocyclopent[b]indole ring portion of the compounds of the invention:

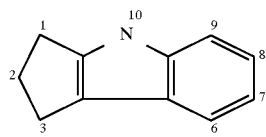

The following numbering system is used to identify positions on the hexahydrocyclohept[b]indole ring portion of the compounds of the invention:

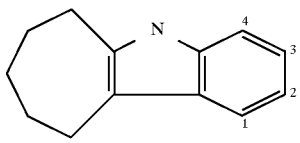

By "alkyl" and "lower alkyl" is meant straight or branched chain alkyl groups having from 1–6 carbon atoms, e.g., $C_1$–$C_6$ alkyl.

By "lower alkoxy" and "alkoxy" is meant straight or branched chain alkoxy groups having from 1–6 carbon atoms, e.g., $C_1$–$C_6$ alkoxy.

By halogen is meant an atom of fluorine, chlorine, bromine or iodine.

The amino portion of the aminoalkyl group represented by $R_p$ above includes groups represented by the formula T

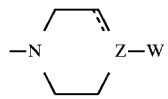

where W is defined above.

The formula T represents saturated heterocyclic ring systems such as, for example, piperidinyl and piperazinyl, as well as unsaturated heterocyclic ring systems such as, for example, 1, 2, 3, 6-tetrahydropyrinine. Preferred T groups are the following:

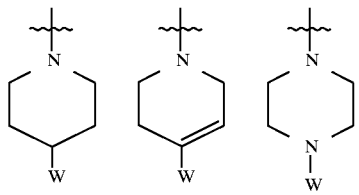

where W is defined above.

Particularly preferred W groups of the invention are quinolinyl, naphthyl, or phenyl optionally substituted with up to two substituents independently selected from halogen, $C_1$–$C_4$ alkyl, and $C_1$–$C_4$ alkoxy. These optional phenyl substituents are preferably in the 2 and/or 3 positions of the phenyl group relative to the point of attachment of the phenyl group to the 6-membered nitrogen containing ring.

Representative examples of fused indolecarboxamides according to the invention are shown in Table 1 below. The number below each compound is its compound number. Each of these compounds may be prepared according to the general reaction scheme set forth below.

The compounds in Table 1 have the following general Formula A:

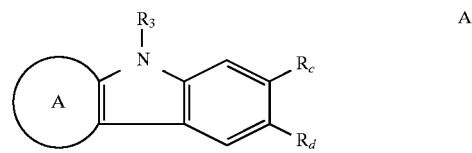

where $R_c$ and $R_d$ independently represent hydrogen or a group of the formula

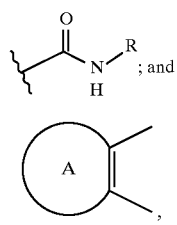

R, $R_3$, and $R_4$ are defined in the table.

TABLE 1

| Compound Number | A | $R_c$ | $R_d$ | $R_3$ | R |
|---|---|---|---|---|---|
| 1 | cyclohexenyl | H | –C(O)NHR | H | –(CH$_2$)$_4$–N(piperazinyl)–2,3-dichlorophenyl |
| 2 | phenyl | H | –C(O)NHR | H | –(CH$_2$)$_4$–N(piperazinyl)–2,3-dichlorophenyl |

TABLE 1-continued

| Compound Number | A | $R_c$ | $R_d$ | $R_3$ | R |
|---|---|---|---|---|---|
| 3 | phenyl | H | -C(O)NH-R | CH₃ | -(CH₂)₄-N(piperazine)N-(2,3-dichlorophenyl) |
| 4 | phenyl | -C(O)NH-R | H | H | -(CH₂)₄-N(piperazine)N-(2,3-dichlorophenyl) |
| 5 | phenyl | -C(O)NH-R | H | CH₃ | -(CH₂)₄-N(piperazine)N-(2,3-dichlorophenyl) |
| 6 | cyclopentenyl | H | -C(O)NH-R | H | -(CH₂)₄-N(piperazine)N-(2,3-dichlorophenyl) |
| 7 | cycloheptenyl | H | -C(O)NH-R | H | -(CH₂)₄-N(piperazine)N-(2,3-dichlorophenyl) |
| 8 | phenyl | -C(O)NH-R | H | H | -(CH₂)₄-N(piperazine)N-(2,3-dimethylphenyl) |
| 9 | phenyl | H | -C(O)NH-R | CH₃ | -(CH₂)₄-N(piperazine)N-(2-methyl-3-chlorophenyl) |
| 10 | phenyl | -C(O)NH-R | H | H | -(CH₂)₄-N(piperazine)N-(2-methyl-3-chlorophenyl) |

The invention also pertains to the use of compounds of general Formula I in the treatment of neuropsychological disorders. The pharmaceutical utility of compounds of this invention are indicated by the following assays for dopamine receptor subtype affinity.

ASSAY FOR $D_2$ AND $D_3$ RECEPTOR BINDING ACTIVITY

Pellets of COS cells containing recombinantly produced $D_2$ or $D_3$ receptors from African Green monkey were used for the assays. The sample is homogenized in 100 volumes (w/vol) of 0.05M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.4 ml of tissue sample, 0.5 nM ³H-YM 09151-2 and the compound of interest in a total incubation of 1.0 ml. Nonspecific binding is defined as that binding found in the presence of 1 mM spiperone; without further additions, nonspecific binding is less than 20% of total binding. The binding characteristics of representative compounds of the invention for $D_2$ and $D_3$ receptor subtypes are shown in Table 2 for rat striatal homogenates.

TABLE 2

| Compound Number[1] | $D_3K_i$ (nM) | $D_2K_i$ (nM) |
|---|---|---|
| 1 | 0.5 | 250 |
| 3 | 2 | 540 |
| 4 | 1 | 750 |

[1]Compound numbers relate to compounds shown above in Table 1.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydlides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the and partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of N-aminoalkyldibenzofurancarboxamides

The compounds of the invention and their corresponding pharmaceutically acceptable acid addition salts thereof may be prepared according to the reactions shown below in the following schemes.

The compounds of Formula I may be prepared by a process which comprises reacting a compound of Formula V with a compound of Formula VI as shown below:

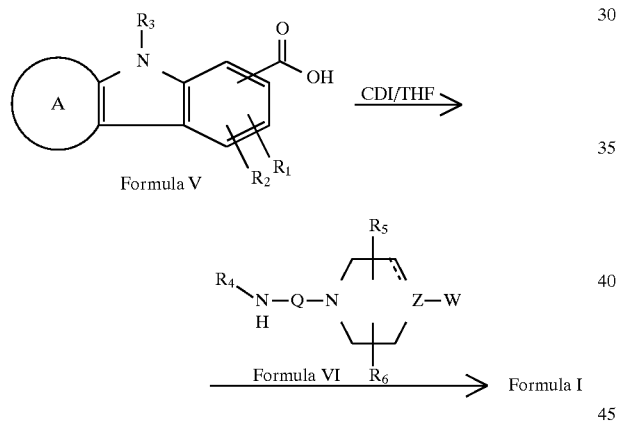

wherein $R_1$, $R_2$, $R_3$, $R_4$, $R_5$, A, Q, Z and W are defined as above for Formula I.

A compound of Formula V may be activated with a reagent such as 1,1'-carbonyldiimidazole (CDI) or the like in a solvent such as tetrahydrofuran or the like at room temperature. The resulting activated carboxylate intermediate may be subsequently reacted with a compound of Formula VI to afford a compound of Formula I as the desired product.

A compound of Formula Va

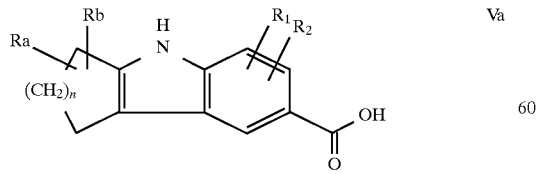

wherein $R_a$, $R_b$, $R_1$, $R_2$ and n are defined as above, may be prepared by reacting a compound of Formula Va1 with a compound of Formula Va2 via the Fischer indole synthesis as shown below:

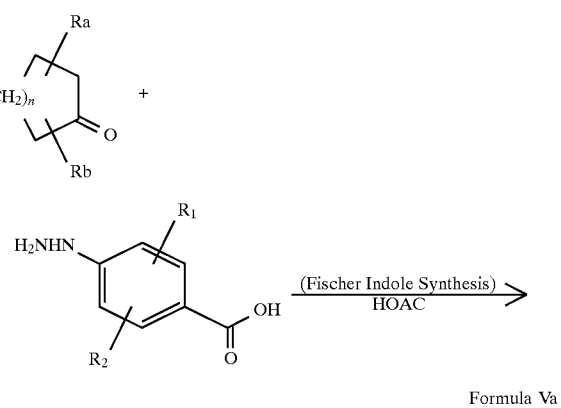

wherein $R_a$, $R_b$, $R_1$, $R_2$ and n are defined as above.

The reaction may be carried out according to procedures well described in the literature. For example, see Robinson, "The Fischer Indole Synthesis", Wiley, N.Y., 1983. Preferably, the reaction is carried out in the presence of acetic acid (HOAC) under reflux for about four hours.

In the case where n is 2, a compound of Formula Va3 may be prepared as depicted in the scheme below by dehydrogenation of a compound of Formula Va in a refluxing solvent such as xylene or the like in the presence of a catalyst such as, for example, palladium on carbon. Preferably, the reaction is carried out with 10% palladium on carbon in xylene at reflux for about eight hours.

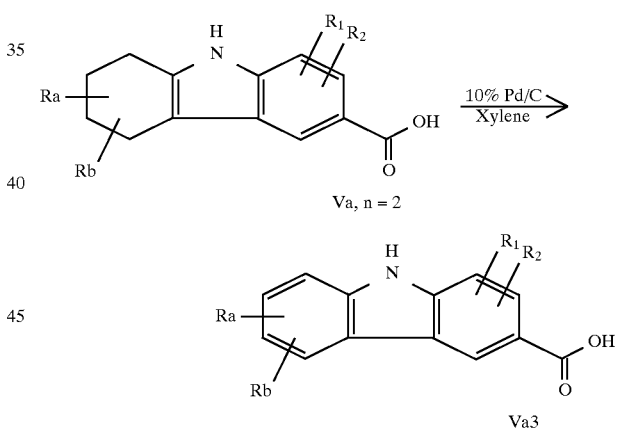

Similarly, a compound of Formula Vb

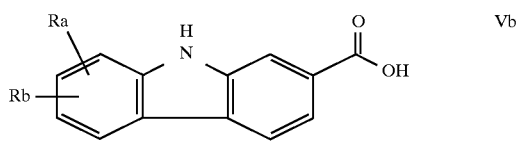

wherein $R_a$ and $R_b$ are defined as above for Formula I, may be prepared by dehydrogenation of a compound of Formula Vb1 as shown in the below scheme in a refluxing solvent such as, for example, xylene, in the presence of a catalyst such as palladium on carbon or the like. Preferably, the reaction is carried out with 10% palladium on carbon in xylene at reflux for about eight hours.

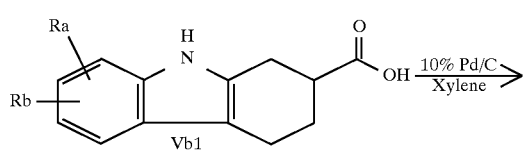

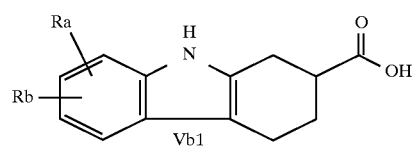

Further, a compound of Formula Vb1

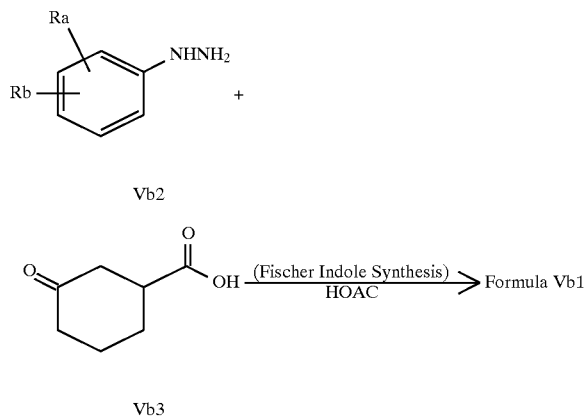

wherein $R_a$ and $R_b$ are defined as above for Formula I, may be prepared by reacting a compound of Formula Vb2 with a compound of Formula Vb3 via the Fischer indole synthesis as represented below:

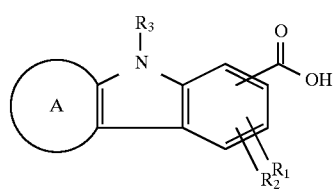

wherein $R_a$ and $R_b$ are defined as above for Formula I. The reaction may be carried out according to well known literature procedures. See, for example, Robinson, "The Fischer Indole Synthesis", Wiley, N.Y., 1983. Preferably, the above reaction is carried out in the presence of acetic acid (HOAC) under reflux for about 4 hours.

A compound of Formula V

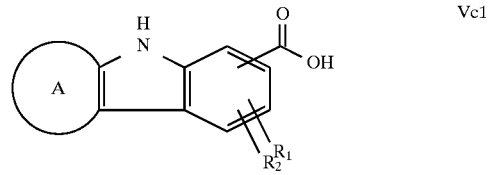

wherein $R_1$, $R_2$ and A are defined as above and $R_3$ is hydrogen, may be prepared by methods analogous to those described above for Formula Va or those for Formula Vb.

Where $R_3$ is not hydrogen, a compound of Formula V may be prepared by reacting a compound of Formula Vc1

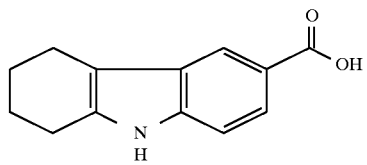

wherein $R_1$, $R_2$ and A are defined as above with a halide of the formula: $R_3$-X, where $R_3$ is defined as above for Formula I and X is a halide. The reaction is normally carried out in the presence of a base such as, for example, $K_2CO_3$ in a solvent such as acetone or the like at room temperature. Subsequently, the resulting intermediate may be hydrolyzed with a base such as NaOH or the like in an aqueous solvent such as methanol at about 50° C. to afford a compound of Formula V. Preferably, the reaction is carried out with $K_2CO_3$ in acetone, and the hydrolysis is carried out with NaOH in aqueous methanol.

Where they are not commercially available, the compounds of Formula Va1, Formula Va2, Formula Vb2 and Formula Vb3 may be prepared by procedures analogous to these described in literature. Compounds of Formula VI often can be obtained from commercial sources. Attentively, such compounds are known compounds or are capable of being prepared by literature methods.

Those having skill in the art will recognize that the starting materials may be varied and additional steps employed to produce compounds encompassed by the present invention, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them. These examples illustrate the presently preferred methods for preparing the compounds of the invention.

EXAMPLE 1

1. 1, 2, 3, 4-tetrahydrocarbazole-6-carboxylic acid

A mixture of 4-hydrazinobenzoic acid (5.0 g, 32.9 mmol) and cyclohexanone (3.3 g, 33 mmol) in 30 mL of acetic acid was heated under reflux for 4 hours, then cooled, diluted with water and acidified with HCl. The resultant solid was collected by filtration, washed with water and dried to give 3.6 g of the title compound as a crystalline solid.

2. N-(1-{4-[4-(2,3-dichlorophenyl)piperazine-1-yl]}butyl)-1,2,3 4-tetrahydrocarbazole-6-carboxamide hydrochloride

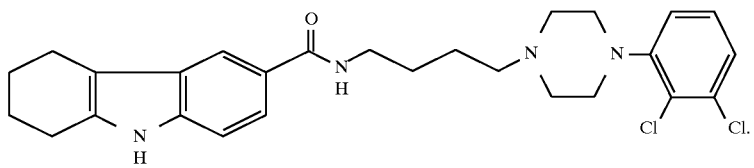

(Compound 1)

A mixture of 1, 2, 3, 4-tetrahyrocarbazole-6-carboxylic acid (100 mg, 0.46 mmol) and 1,1'-carbonyldiimidazole (78 mg, 0.48 mmol) in 5 mL of anhydrous tetrahydrofuran was stirred for 8 hours. A solution of 4-[4-(2,3-dichlorophenyl)piperazine-1-yl]-1-aminobutane (140 mg, 0.46 mmol) in 1 mL of tetrahydrofuran was added and the resulting mixture was stirred for 30 minutes. The reaction mixture was partitioned between ethyl acetate and water. The organic layer was washed with aqueous $Na_2CO_3$ solution, dried ($Na_2SO_4$) and concentrated in vacuo to afford the free base of the title compound, N-(1-{4-[4-(2,3-dichlorophenyl)piperazine-1-yl]}butyl)-1,2,3,4-tetrahydrocarbazole-6-carboxamide, (161 mg, 70%). The hydrochloride salt was prepared by treating the free base with a solution of hydrogen chloride in ethyl acetate (mp 236°–238° C.).

EXAMPLE 2

The following compounds are prepared essentially according to the procedures set forth in Example 1 above.

(a) N-(1-{4-[4-(3-Chloro-2-methylphenyl)piperazine-1-yl]}butyl)-1, 2, 3, 4-tetrahydrocarbazole-6-carboxamide hydrochloride (mp 229°–231° C.)

(b) N-(1-{4-[4-(2,3-Dimethylphenyl)piperazine-1-yl]}butyl)-1, 2, 3, 4-tetrahydrocarbazole-6-carboxamide hydrochloride (mp 224°–226° C.)

(c) N-(1-{4-[4-(1-Naphthyl)piperazine-1-yl]}butyl)-1, 2, 3, 4-tetrahydrocarbazole-6-carboxamide hydrochloride (mp 207°–210° C.)

(d) N-(1-{4-[4-(2,3-Dichlorophenyl)piperazine-1-yl]}butyl)-1, 2, 3, 4-tetrahydrocyclopent[b]indole-7-carboxamide hydrochloride (Compound 6, mp 224°–226° C.)

(e) N-(1-{4-[4-(3-Chloro-2-methylphenyl)piperazine-1-yl]}butyl)-1, 2, 3, 4-tetrahydro-cyclopent[b]indole-7-carboxamide hydrochloride (mp 231°–233° C.)

(f) N-(1-{4-[4-(2,3-Dichlorophenyl)piperazine-1-yl]}butyl)-5,6,7,8,9,10-hexalhydrocyclohept[b]indole-2-carboxamide (Compound 7, mp 212°–214° C.)

EXAMPLE 3

1. Preparation of 9H-carbazole-3-carboxylic acid.

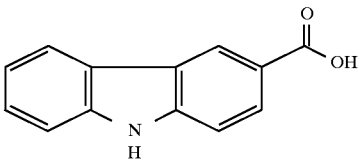

A suspension of 1, 2, 3, 4-tetrahydrocarbazole-6-carboxylic acid (1.0 g, 4.6 mmol) and 10% Pd/C (0.7 g) in 50 mL of xylene was heated under reflux for 8 hours. The hot reaction mixture was filtered through celite. The filtrate was concentrated in vacuo to give the title compound (0.8 g, 80%).

2. N-(1-{4-[4-(2,3-dichlorophenyl)piperazine-1-yl]}butyl)-9H-carbazole-3-carboxamide hydrochloride

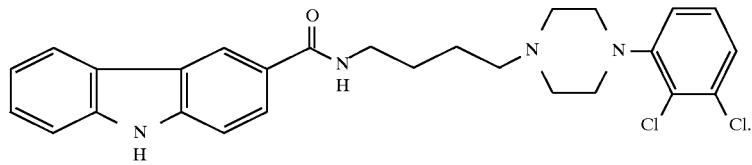

(Compound 2)

A mixture of 9H-carbazole-3-carboxylic acid (50 mg, 0.23 mmol) and 1,1'-carbonyldiimidazole (39 mg, 0.24 mmol) in 5 mL of anhydrous tetrahydrofuran was stirred for 8 hours. A solution of 4-[4-(2,3-dichlorophenyl)piperazine-1-yl]-1-aminobutane 70 mg, 0.23 mmol) in 1 mL of tetrahydrofuran was added and the resulting mixture was stirred for 30 minutes. The reaction mixture was partitioned between ethyl acetate and water. The organic layer was washed with aqueous $Na_2CO_3$ solution, dried ($Na_2SO_4$) and concentrated in vacuo to give the title compound (85 mg, 72%). The hydrochloride salt was prepared by treating the free base with a solution of hydrogen chloride in ethyl acetate (mp 214°–216° C.).

EXAMPLE 4

The following compounds are prepared essentially according to the procedures set forth above in Example 3.

(a) N-(1-{4-[4-(2,3-Dimethylphenyl)piperazine-1-yl]}butyl)-9H-carbazole-3-carboxamide hydrochloride (mp 218°–220° C.)

(b) N-(1-{4-[4-(1-Naphthyl)piperazine-1-yl]}butyl)-9H-carbazole-3-carboxamide hydrochloride (mp 225°–227° C.)

EXAMPLE 5

1. 1,2,3,4-tetrahydrocarbazole-2-carboxylic acid

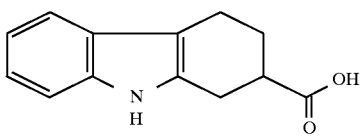

A mixture of 3-ketocyclohexanecarboxylic acid (4.78 g, 33.9 mmol) and phenyihydrazine (3.66 g, 40 mmol) in 35 mL of acetic acid was heated under reflux for one hour, then cooled, diluted with water and acidified with HCl. The resultant solid was collected by filtration, washed with water and dried to give 5.5 g of the title compound as a crystalline solid.

2. 9H-carbazole-2-carboxylic acid

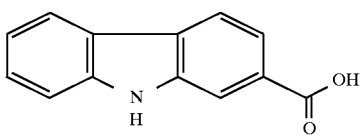

A suspension of 1,2,3,4-tetrahydrocarazole-2-carboxylic acid (0.6 g, 2.8 mmol) and 10% Pd/C (0.5 g) in 30 mL of xylene was heated under reflux for 8 hours. The hot reaction mixture was filtered through celite. The filtrate was concentrated in vacuo to give the title compound (0.5 g, 85%)

3. N-(1-{4-[4-(2,3-dichlorophenyl)piperazine-1-yl]}butyl)-9H-carbazole-2-carboxamide hydrochloride

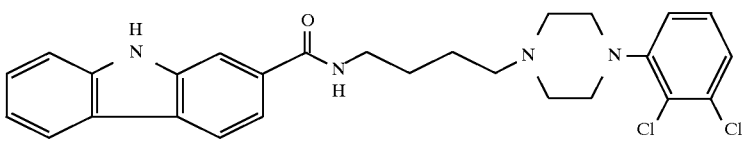

A mixture of 9H-carbazole-2-carboxylic acid (50 mg, 0.23 mmol) and 1,1'-carbonyldiimidazole (39 mg, 0.24 mmol) in 5 mL of anhydrous tetrahydrofuran was stirred for 8 hours. A solution of 4-[4-(2,3-dichlorophenyl)piperazine-1-yl]-1-aminobutane (70 mg, 0.23 mmol) in 1 mL of tetrahydrofuran was added and the resulting mixture was stirred for 30 minutes. The reaction mixture was partitioned between ethyl acetate and water. The organic layer was washed with aqueous $Na_2CO_3$ solution, dried ($Na_2SO_4$) and concentrated in vacuo to give the title compound (75 mg, 64%). The hydrochloride salt was prepared by treating the free base with a solution of hydrogen chloride in ethyl acetate (mp 240°–241° C.).

EXAMPLE 6

The following compounds are prepared essentially according to the procedures set forth above in Example 5.

(a) N-(1-{4-[4-(2,3-Methylphenyl)piperazine-1-yl]}butyl)-9H-carbazole-2-carboxamide hydrochloride (Compound 8, mp 250°–253° C.)

(b) N-(1-{4-[4-(3-Chloro-2-methylphenyl)piperazine-1-yl]}butyl)-9H-carbazole-2-carboxamide hydrochloride (Compound 10, mp 246°–248° C.)

EXAMPLE 7

1. 9-methylcarbazole-3-carboxylic acid

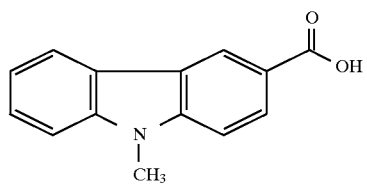

A mixture of 9H-carbazole-3-carboxylic acid (300 mg, 1.42 mmol), $K_2CO_3$ (800 mg) and methyl iodide (1 mL) in 25 mL of acetone was heated under reflux overnight, then cooled and evaporated in vacuo. A mixture of the resultant residue and NaOH (170 mg) in aqueous MeOH (90%, 25 mL) was stirred at 50° C. for 30 minutes. The reaction mixture was concentrated and acidified with diluted HCl. The solids were collected by filtration and dried to give the title compound (280 mg, 87%).

2. N-(1-{4-[4-(2,3-dichlorophenyl)piperazine-1-yl]}butyl)-9-methylcarbazole-3-carboxamide hydrochloride

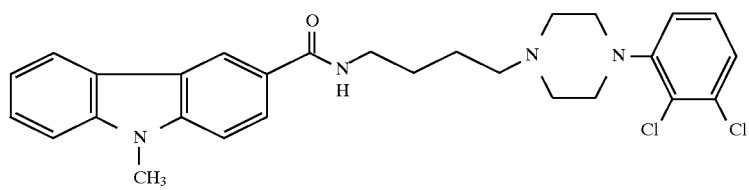

(Compound 3)

A mixture of 9H-carbazole-2-carboxylic acid (50 mg, 0.23 mmol) and 1,1'-carbonyldiimidazole (39 mg, 0.24 mmol) in 5 mL of anhydrous tetrahydiofuran was stirred for 8 hours. A solution of 4-[4-(2,3-dichlorophenyl)piperazine-1-yl]-1-aminobutane (70 mg, 0.23 mmol) in 1 mL of tetrahydrofuran was added and the resulting mixture was stirred for 30 minutes. The reaction mixture was partitioned between ethyl acetate and water. The organic layer was washed with aqueous $Na_2CO_3$ solution, dried ($Na_2SO_4$) and concentrated in vacuo to give the title compound (80 mg, 68%). The hydrochloride salt was prepared by treating the free base with a solution of hydrogen chloride in ethyl acetate (mp 237°–239° C.).

EXAMPLE 8

The following compounds are prepared essentially according to the procedures set forth above in Example 7.

(a) N-(1-{4-[4-(3-Chloro-2-methylphenyl)piperazine-1-yl]}butyl)-9-methylcarbazole-3-carboxamide hydrochloride (mp 224°–226° C.)

(b) N-(1-{4-[4-(2,3-Dichlorophenyl)piperazine-1-yl]}butyl)-9-methylcarbazole-2-carboxamide hydrochloride (Compound 5, mp 276°–78° C.)

(c) N-(1-{4-[4-(3-Chloro-2-methylphenyl)piperazine-1-yl]}butyl)-9-methylcarbazole-2-carboxamide hydrochloride (Compound 9, mp 269°–271° C.)

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

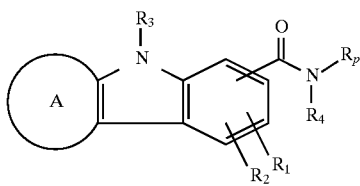

or the pharmaceutically acceptable salts thereof wherein

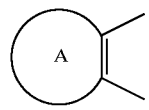

represents

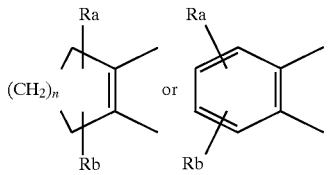

where $R_a$ and $R_b$ independently represent hydrogen, $C_1$–$C_6$ alkyl, hydroxy, $C_1$–$C_6$ alkoxy, or amino mono- or disubstituted with $C_1$–$C_6$ alkyl; and n is an integer from one to four;

$R_1$ and $R_2$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —SO$_m$R', where R' is $C_1$–$C_6$ alkyl and wherein m is 0, 1 or 2; or $R_1$ and $R_2$ independently represent —CONR'R", or —NR'R" where R' and R" independently represent hydrogen or $C_1$–$C_6$ alkyl;

$R_3$ is hydrogen, $C_1$–$C_6$ alkyl, or —COR''' where R''' is $C_1$–$C_6$ alkyl;

$R_4$ is hydrogen or $C_1$–$C_6$ alkyl; and Rp represents a group of the formula

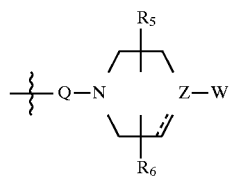

where

Q represents an alkylene group of 2 to 6 carbon atoms optionally substituted with one or more alkyl groups having from 1 to 4 carbon atoms;

Z is N whereby . . . is a single bond;

$R_5$ and $R_6$ are the same or different and represent hydrogen or $C_1$–$C_6$ alkyl; and W is phenyl, naphthyl, 1-(5,6,7,8-tetrahydro)naphthyl or 4-(1,2-dihydro)indenyl, quinolinyl, pyridinyl, pyrimidyl, isoquinolinyl, benzofuranyl, benzothienyl; each of which is optionally substituted with up to three groups independently selected from halogen, $C_1$–$C_6$ alkyl, $C_1$–$C_4$ alkoxy, thioalkoxy, hydroxy, amino, monoalkylamino, dialkylamino, cyano, nitro, trifluoromethyl or trifluoromethoxy.

2. A compound of the formula:

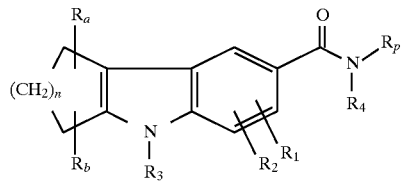

wherein $R_a$ and $R_b$ independently represent hydrogen, $C_1$–$C_6$ alkyl, hydroxy, $C_1$–$C_6$ alkoxy, or amino mono- or disubstituted with $C_1$–$C_6$ alkyl; and n is an integer from one to four;

$R_1$ and $R_2$ are the same or different and represent hydrogen, $C_1$–$C_6$ alkyl, halogen, hydroxy, amino, cyano, nitro, trifluoromethyl, trifluoromethoxy, $C_1$–$C_6$ alkoxy, —$O_2CR'$, —NHCOR', —COR', —SO$_m$R', where R' is $C_1$–$C_6$ alkyl and wherein m is 0, 1 or 2; or $R_1$ and $R_2$ independently represent —CONR'R", or —NR'R" where R' and R" independently represent hydrogen or $C_1$–$C_6$ alkyl;

$R_3$ is hydrogen, $C_1$–$C_6$ alkyl, or —COR''' where R''' is $C_1$–$C_6$ alkyl;

$R_4$ is hydrogen or $C_1$–$C_6$ alkyl; and $R_p$ represents a group of the formula

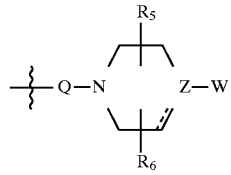

where

Q represents an alkylene group of 2 to 6 carbon atoms optionally substituted with one or more alkyl groups having from 1 to 4 carbon atoms;

Z is N whereby . . . is a single bond;

$R_5$ and $R_6$ are the same or different and represent hydrogen or $C_1$–$C_6$ alkyl; and W is phenyl, naphthyl, 1-(5,6,7,8-tetrahydro)naphthyl or 4-(1,2-dihydro)indenyl, quinolinyl, pyridinyl, pyrimidyl, isoquinolinyl, benzofuranyl, benzothienyl; each of which is optionally substituted with up to three groups independently selected from halogen, $C_1-C_6$ alkyl, $C_1-C_4$ alkoxy, thioalkoxy, hydroxy, amino, monoalkylamino, dialkylamino, cyano, nitro, trifluoromethyl or trifluoromethoxy.

3. A compound of the formula:

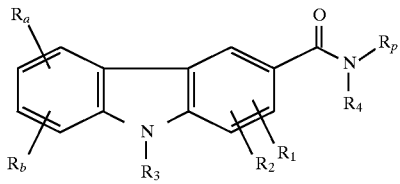

wherein $R_a$ and $R_b$ independently represent hydrogen, $C_1-C_6$ alkyl, hydroxy, $C_1-C_6$ alkoxy, or amino mono- or disubstituted with $C_1-C_6$ alkyl; and $R_1$ and $R_2$ are the same or different and represent hydrogen, $C_1-C_6$ alkyl, halogen, hydroxy, amino, cyano, nitro, trifluoromethyl, trifluoromethoxy, $C_1-C_6$ alkoxy, —$O_2CR'$, —NHCOR', —COR', —$SO_mR'$, where R' is $C_1-C_6$ alkyl and wherein m is 0, 1 or 2; or $R_1$ and $R_2$ independently represent —CONR'R", or —NR'R" where R' and R" independently represent hydrogen or $C_1-C_6$ alkyl;

$R_3$ is hydrogen, $C_1-C_6$ alkyl, or —COR'" where R'" is $C_1-C_6$ alkyl;

$R_4$ is hydrogen or $C_1-C_6$ alkyl; and $R_p$ represents a group of the formula

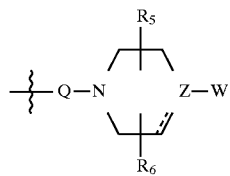

where

Q represents an alkylene group of 2 to 6 carbon atoms optionally substituted with one or more alkyl groups having from 1 to 4 carbon atoms;

Z is N whereby . . . is a single bond;

$R_5$ and $R_6$ are the same or different and represent hydrogen or $C_1-C_6$ alkyl; and W is phenyl, naphthyl, 1-(5,6,7,8-tetrahydro)naphthyl or 4-(1,2-dihydro)indenyl, quinolinyl, pyridinyl, pyrimidyl, isoquinolinyl, benzofuranyl, benzothienyl; each of which is optionally substituted with up to three groups independently selected from halogen, $C_1-C_6$ alkyl, $C_1-C_4$ alkoxy, thioalkoxy, hydroxy, amino, monoalkylamino, dialkylamino, cyano, nitro, trifluoromethyl or trifluoromethoxy.

4. A compound of the formula:

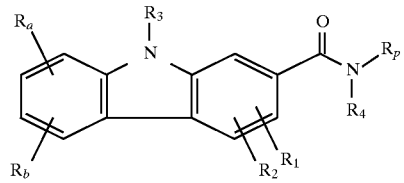

wherein $R_a$ and $R_b$ independently represent hydrogen, $C_1-C_6$ alkyl, hydroxy, $C_1-C_6$ alkoxy, or amino mono- or disubstituted with $C_1-C_6$ alkyl; and $R_1$ and $R_2$ are the same or different and represent hydrogen, $C_1-C_6$ alkyl, halogen, hydroxy, amino, cyano, nitro, trifluoromethyl, trifluoromethoxy, $C_1-C_6$ alkoxy, —$O_2CR'$, —NHCOR', —COR', —$SO_mR'$, where R' is $C_1-C_6$ alkyl and wherein m is 0, 1 or 2; or $R_1$ and $R_2$ independently represent —CONR'R", or —NR'R" where R' and R" independently represent hydrogen or $C_1-C_6$ alkyl;

$R_3$ is hydrogen, $C_1-C_6$ alkyl, or —COR'" where R'" is $C_1-C_6$ alkyl;

$R_4$ is hydrogen or $C_1-C_6$ alkyl; and $R_p$ represents a group of the formula

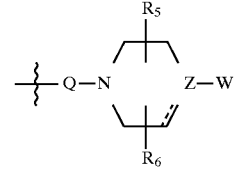

where

Q represents an alkylene group of 2 to 6 carbon atoms optionally substituted with one or more alkyl groups having from 1 to 4 carbon atoms;

Z is N whereby . . . is a single bond;

$R_5$ and $R_6$ are the same or different and represent hydrogen or $C_1-C_6$ alkyl; and W is phenyl, naphthyl, 1-(5,6,7,8-tetrahydro)naphthyl or 4-(1,2-dihydro)indenyl, quinolinyl, pyridinyl, pyrimidyl, isoquinolinyl, benzofuranyl, benzothienyl; each of which is optionally substituted with up to three groups independently selected from halogen, $C_1-C_6$ alkyl, $C_1-C_4$ alkoxy, thioalkoxy, hydroxy, amino, monoalkylamino, dialkylamino, cyano, nitro, trifluoromethyl or trifluoromethoxy.

5. A compound according to claim 1, whererin Q is alkylene of 3–5 carbon atoms and $R_1$ and $R_2$ are hydrogen.

6. A compound according to claim 2, whererin Q is alkylene of 3–5 carbon atoms and $R_1$ and $R_2$ are hydrogen.

7. A compound according to claim 3, whererin Q is alkylene of 3–5 carbon atoms and $R_1$ and $R_2$ are hydrogen.

8. A compound according to claim 4, whererin Q is alkylene of 3–5 carbon atoms and $R_1$ and $R_2$ are hydrogen.

9. A compound according to claim 5, whererin Q is butylene.

10. A compound according to claim 2, which is N-(1-{4-[4-(2,3-dichlorophenyl)piperazine-1-yl]}butyl)-1, 2, 3, 4-tetrahydrocarbazole-6-carboxamide hydrochloride.

11. A compound according to claim 2, which is N-(1-{4-[4-(3-Chloro-2-methylphenyl)piperazine-1-yl]}butyl)-1, 2, 3, 4-tetrahydrocarbazole-6-carboxamide hydrochloride.

12. A compound according to claim 2, which is N-(1-{4-[4-(2,3-Dimethylphenyl)piperazine-1-yl]}butyl)-1, 2, 3, 4-tetrahydrocarbazole-6-carboxamide hydrochloride.

13. A compound according to claim 2, which is N-(1-{4-[4-(1-Naphthyl)piperazine-1-yl]}butyl)-1, 2, 3, 4-tetrahydrocarbazole-6-carboxamide hydrochloride.

14. A compound according to claim 2, which is N-(1-{4-[4-(2,3-Dichlorophenyl)piperazine-1-yl]}butyl)-5,6,7,8-tetrahydrocyclopent[b]indole-7-carboxamide hydrochloride.

15. A compound according to claim 2, which is N-(1-{4-[4-(3-Chloro-2-methylphenyl)piperazine-1-yl]}butyl)-5,6,7,8-tetrahydrocyclopent[b]indole-7-carboxamide hydrochloride.

16. A compound according to claim 2, which is N-(1-{4-[4-(2,3-Dichlorophenyl)piperazine-1-yl]}butyl)-5,6,7,8,9,10-hexahydrocyclohept[b]indole-2-carboxamide.

17. A compound according to claim 2, which is N-(1-{4-[4-(2,3-Dichlorophenyl)piperazine-1-yl]}butyl)-9H-carbazole-3-carboxamide hydrochloride.

18. A compound according to claim 2, which is N-(1-{4-[4-(2,3-Dimethylphenyl)piperazine-1-yl]}butyl)-9H-carbazole-3-carboxamide hydrochloride.

19. A compound according to claim 2, which is N-(1-{4-[4-(2,3-Dichlorophenyl)piperazine-1-yl]}butyl)-9-methylcarbazole-3-carboxamide hydrochloride.

20. A compound according to claim 2, which is N-(1-{4-[4-(3-Chloro-2-methylphenyl)piperazine-1-yl]}butyl)-9-methylcarbazole-3-carboxamide hydrochloride.

21. A compound according to claim 2, which is N-(1-{4-[4-(2,3-Dichlorophenyl)piperazine-1-yl]}butyl)-9H-carbazole-2-carboxamide hydrochloride.

22. A compound according to claim 2, which is N-(1-{4-[4-(2,3-Methylphenyl)piperazine-1-yl]}butyl)-9H-carbazole-2-carboxamide hydrochloride.

23. A compound according to claim 2, which is N-(1-{4-[4-(3-Chloro-2-methylphenyl)piperazine-1-yl]}butyl)-9H-carbazole-2-carboxamide hydrochloride.

24. A compound according to claim 2, which is N-(1-{4-[4-(2,3-Dichlorophenyl)piperazine-1-yl]}butyl)-9-methylcarbazole-2-carboxamide hydrochloride.

25. A compound according to claim 2, which is N-(1-{4-[4-(3-Chloro-2-methylphenyl)piperazine-1-yl]}butyl)-9-methylcarbazole-2-carboxamide hydrochloride.

* * * * *